(12) United States Patent
Chen et al.

(10) Patent No.: US 9,156,790 B2
(45) Date of Patent: Oct. 13, 2015

(54) ANTICANCER P21-ACTIVATED KINASE INHIBITORS

(71) Applicant: Ohio State Innovation Foundation, Columbus, OH (US)

(72) Inventors: Ching-Shih Chen, Upper Arlington, OH (US); Matthew David Ringel, Columbus, OH (US); Motoyashi Saji, Dublin, OH (US); Yihui Ma, Zhenghou (CN)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/230,689

(22) Filed: Mar. 31, 2014

(65) Prior Publication Data

US 2014/0323538 A1    Oct. 30, 2014

Related U.S. Application Data

(60) Provisional application No. 61/806,518, filed on Mar. 29, 2013.

(51) Int. Cl.
| | |
|---|---|
| *A61K 31/415* | (2006.01) |
| *C07D 231/12* | (2006.01) |
| *C07D 231/14* | (2006.01) |

(52) U.S. Cl.
CPC ............ *C07D 231/12* (2013.01); *A61K 31/415* (2013.01); *C07D 231/14* (2013.01)

(58) Field of Classification Search
CPC .............................. C07D 231/12; A61K 31/415
See application file for complete search history.

(56) References Cited

U.S. PATENT DOCUMENTS

| | | | | |
|---|---|---|---|---|
| 7,576,116 | B2 * | 8/2009 | Chen | 514/406 |
| 8,080,574 | B2 * | 12/2011 | Chen | 514/406 |
| 8,541,460 | B2 * | 9/2013 | Chen | 514/406 |
| 8,546,441 | B2 * | 10/2013 | Chen | 514/406 |

OTHER PUBLICATIONS

Chen, Su-Lin Lee. Identification and Characterization of a Novel Integrin-Linked Kinase Inhibitor. Journal of Medicinal Chemistry. 2011, 54, 6364-6374.*

* cited by examiner

*Primary Examiner* — Samantha Shterengarts
(74) *Attorney, Agent, or Firm* — Tarolli, Sundheim, Covell & Tummino LLP; Raymond N. Russell

(57) ABSTRACT

Compounds according to formula I:

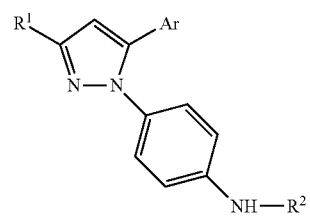

wherein Ar is a fused aryl group, $R^1$ is selected from alkyl and aryl amides, $CF_3$, and $CH_2OH$, and $R_2$ is selected from hydrogen, —C(=O)$CH_2NH_2$, and —C(=O)$CH_2CH_2NH_2$ are described. The compounds are effective for inhibiting p21-activated kinases, and can be used for prevention and treatment of cancer.

10 Claims, 8 Drawing Sheets

A. SERIES I (1, 2, 7, 9, 11, 13, 15 - 17)

ANTICANCER P21-ACTIVATED KINASE INHIBITORS

CROSS-REFERENCE TO RELATED APPLICATIONS

This application claims priority to U.S. Provisional Application Ser. No. 61/806,518; filed on Mar. 29, 2013, which is incorporated herein by reference in its entirety.

STATEMENT REGARDING FEDERALLY SPONSORED RESEARCH

The present invention was supported by NIH grants CA124570-04 and CA112250. The Government has certain rights in this invention.

BACKGROUND p21-activated kinases (PAKs) are a family of downstream effectors of small GTPase cdc42 and rac that function as central regulators of cell motility and cytoskeletal rearrangement. Six unique PAK isoforms have been cloned that are divided into two groups, PAKs 1-3 and PAKs 4-6, based on the sequence and functional characteristics. As direct targets of Cdc42 and Rac, PAKs participate in a wide range of physiological processes beyond cell motility, including cell proliferation, apoptosis regulation, and in some systems, oncogenesis. PAK activation and overexpression has been identified in a variety of malignancies. In thyroid cancer, an increase in PAK1 expression, pPAK levels, and PAK-mediated phosphorylation of downstream effectors in the invasive fronts in aggressive papillary cancers has been reported. Thus, PAK1 represents an important therapeutic target.

P21 activated kinases (PAK) are regulators of cancer cells' structural integrity and are involved in the initiation of cell motilty and also proliferation. PAK1 is an oncogene in breast cancer and also is involved in regulating resistance of breast cancer to hormonal therapies. PAKs also are regulators of thyroid cancer invasion and progression. They have similar properties for other tumors. Thus, PAK-targeted agents may have a specific role in impairing or reversing cancer progression. To date, there are no PAK inhibitors that are FDA-approved creating an opportunity for development of new therapeutics against this key cancer target.

SUMMARY OF THE INVENTION

Based on an earlier finding that OSU-03012 inhibits PAK1 with high potency (Mol. Pharmacol. 72, 1124-31 (2007)), the inventors embarked on the structural modification of OSU-03012 aiming at improving the potency and selectivity in PAK1 inhibition. OSU-03012 is a multikinase inhibitor that competitively blocks ATP binding of both phosphoinositide dependent kinase 1 (PDK1) and PAK1. This effort led to the development of novel PAK1 inhibitors with higher potency and improved selectivity in kinase inhibition. Seventeen compounds were created by combinatorial chemistry predicted to inhibit PAK activity with reduced anti-PDK1 effect. Two lead compounds were identified based the ability to inhibit PAK1 activity in an ATP-competitive manner without discernible in vivo PDK1 inhibitory activity in thyroid cancer cell lines. Both compounds reduced thyroid cancer cell viability. Although they are not PAK-specific on a multi-kinase screening assay, the anti-migration activity effect of the compounds in thyroid cancer cells was rescued by overexpression of a constitutively active PAK1, suggesting this activity is involved in this biological effect.

Accordingly, one aspect of the invention provides a compound according to formula I:

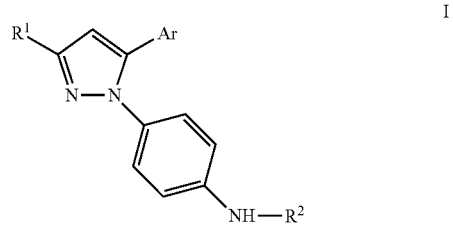

wherein Ar is a fused aryl group, $R^1$ is selected from alkyl and aryl amides, $CF_3$, and $CH_2OH$, and $R_2$ is selected from hydrogen, $-C(=O)CH_2NH_2$, and $-C(=O)CH_2CH_2NH_2$, and pharmaceutically acceptable salts thereof. In further aspects of the invention, the compounds of formula I can be used to inhibit one or more p21-activated kinases, while in additional aspects of the invention, the compounds of formula I can be used to treat or prevent cancer in a subject.

Figure 1:
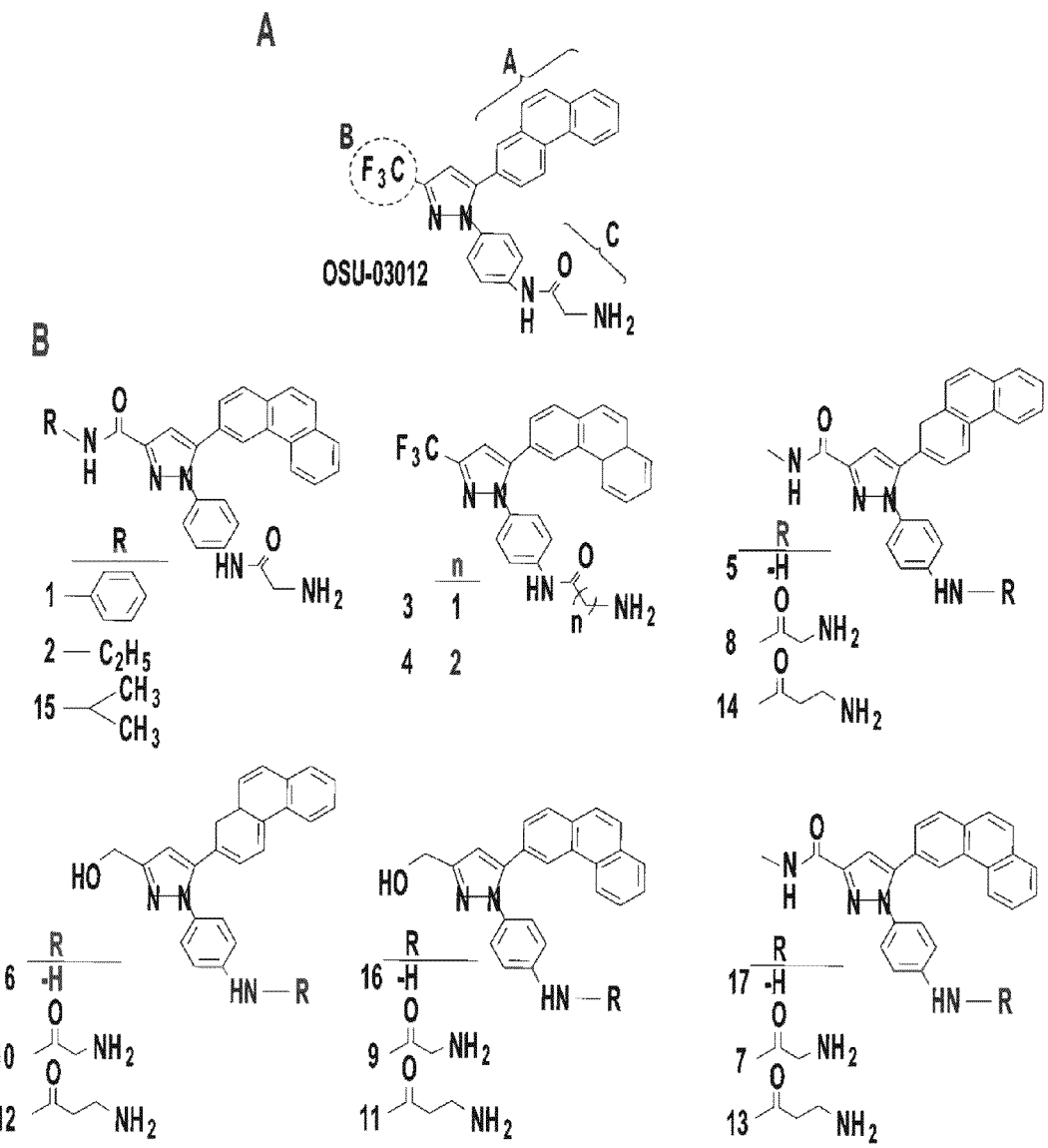
FIG. 1 provides a scheme showing (A) structural modifications of OSU-03012 focused on sites A, B, and C and (B) structures of compounds 1-17.

(a) Diethyl oxalate, CH$_3$ONa, THF; (b) (4-nitrophenyl)hydrazine hydrochloride, TsOH, EtOH; (c) hydrazine, 10% Pd—C; (d) tertbutoxycarbonyl (Boc)-glycine or Boc-j-alanine, 1-ethyl-3-(3-dimethylaminopropyl)-carbodiimide (EDC); (e) RNH$_2$ or CH$_3$NH$_2$/CH$_3$OH; (f) LAH/THF at 0° C.; (g) 3M HCl in CH$_3$OH.

DETAILED DESCRIPTION OF THE INVENTION

The inventors have demonstrated herein that compounds according to formula I exhibit higher potency and/or selectivity as PAK inhibitors, and can also be used as antitumor agents due to the important role played by PAK expression and/or activation in many types of cancer. Thus, using previously developed compound OSU-03012 as a scaffold, the inventors developed a focused compound library, the screening of which led to the identification of useful new compounds.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for compounds of this invention are those that do not interfere with the PAK inhibiting activity of the compounds. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., C$_1$-C$_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

The term "fused aryl group" includes fused carbocyclic aromatic rings or ring systems. Fused aryl groups include a plurality of aromatic rings that are fused to form a single aromatic system. Examples of fused aryl groups include naphthalene (C$_{10}$), anthracene (C$_{14}$), phenanthrene (C$_{14}$) and pyrene (C$_{16}$) fused aryl groups. Collectively, fused aryl groups can be referred to by reference to the number of carbon ring atoms they contain; i.e., a C$_{10}$-C$_{18}$ is carboaryl group.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Additional substituents that can optionally be substituted on a group are further defined below.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$.

Amino: —NR$^1$R$^2$, wherein R$^1$ and R$^2$ are independently amino substituents, for example, hydrogen or a C$_{1-7}$ alkyl group. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

"Pharmaceutically acceptable" as used herein means that the compound or composition is suitable for administration to a subject for the methods described herein, without unduly deleterious side effects in light of the severity of the disease and necessity of the treatment.

The term "therapeutically effective" is intended to qualify the amount of each agent which will achieve the goal of decreasing disease severity while avoiding adverse side effects such as those typically associated with alternative therapies. The therapeutically effective amount may be administered in one or more doses. An effective dose, on the other hand, is an amount sufficient to provide a certain effect, such as enzyme inhibition, but may or may not be therapeutically effective.

In one aspect, the present invention provides a series of compounds according to formula I:

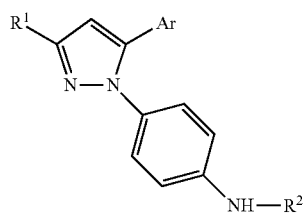

I wherein Ar is a fused aryl group, $R^1$ is selected from alkyl and aryl amides, $CF_3$, and $CH_2OH$, and $R^2$ is selected from hydrogen, —C(═O)$CH_2NH_2$, and —C(═O)$CH_2CH_2NH_2$, and pharmaceutically acceptable salts thereof.

One or more of the substituents of the compounds of formula I can be varied to provide additional embodiments of the invention. The compounds can be varied at different regions of the compounds. For example, the compounds can be varied by changing the group provided at $R^1$ positioned on the pyrazole ring. Alternately, or in addition, the compounds can be varied by changing the group provided at $R^2$, which is adjacent to the amine group provided on the phenyl ring of the compounds. Finally, the compounds can also be varied, again alternately or in addition, by varying the aryl group positioned on the pyrazole ring.

In some embodiments, the fused aryl group Ar is a phenanthrene group. In further embodiments, the fused aryl group Ar is attached at the 3' position of the phanthrene group to provide a 3-phenanthrene group.

In some embodiments, $R^1$ is an alkyl amide, an aryl amide, a trifluoromethyl group, or a hydroxymethyl group. When $R^1$ is an alkyl or aryl amide, the amide group is attached directly to the pyrazole ring through its carbonyl moiety. Preferably, $R^1$ is a bulky alkyl group, which includes alkyl amides, aryl amides, and trifluormethyl groups. In further embodiments, $R^1$ is either a trifluoromethyl group, or is an alkyl or aryl amide. The alkyl portion of alkyl amides is preferably a lower alkyl group including from 1 to 4 carbon atoms.

In some embodiments, $R^2$ is an alkyl carbonyl group, in which the carbonyl is positioned adjacent to the amine of the phenyl group. In further embodiments, the alkyl group of the alkyl carbonyl is a lower alkyl group, and in yet further embodiments the alkyl group of the alkyl carbonyl is an alkyl amine. Examples of preferred $R^2$ groups include —C(═O)$CH_2CH_2NH_2$ and —C(═O)$CH_2NH_2$.

In some embodiments, compounds according to formula I that exhibited higher activity and/or selectivity as a multikinase inhibitor can be selected. In one embodiment, Ar is 3-phenanthrene, $R^1$ is $CF_3$ and $R^2$ is —C(═O)$CH_2CH_2NH_2$, to provide the following compound:

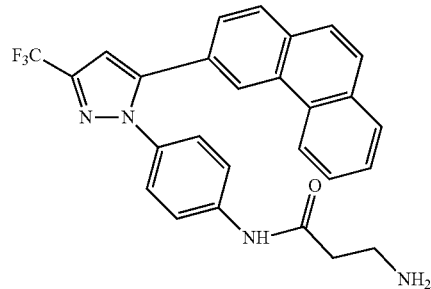 [SMILES: NCCC(=O)Nc1ccc(-n2nc(C(F)(F)F)cc2-c2ccc3ccc4ccccc4c3c2)cc1]

In another embodiment, Ar is 3-phenanthrene, $R^1$ is —C(═O)NH-isopropyl, and $R^2$ is —C(═O)$CH_2NH_2$ to provide the following compound:

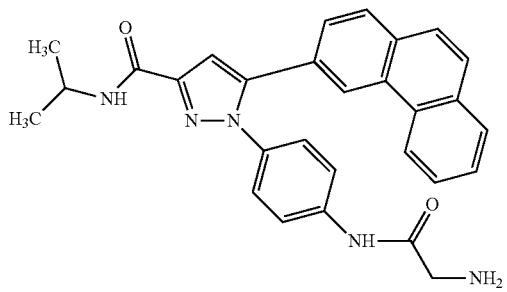 [SMILES: CC(C)NC(=O)c1cc(-c2ccc3ccc4ccccc4c3c2)n(-c2ccc(NC(=O)CN)cc2)n1]

Cancer Treatment Using the Compounds of the Invention

The present invention provides methods for treating or preventing the development of cancer in a subject by administering to the subject a pharmaceutical composition including a compound of formula I or a pharmaceutically acceptable salt thereof. Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as pre-cancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, hepatic cancer, non-small cell lung cancer, colon cancer, central nervous system cancer, melanoma, ovarian cancer, renal cancer, prostate cancer, and breast cancer.

One aspect of the invention provides a method of treating or preventing cancer by administering to a subject a therapeutically effective amount of a compound according to formula I:

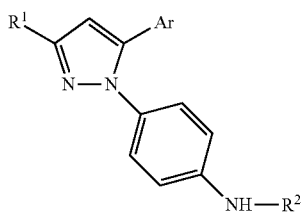

wherein Ar is a fused aryl group, $R^1$ is selected from alkyl and aryl amides, $CF_3$, and $CH_2OH$, and $R^2$ is selected from hydrogen, $-C(=O)CH_2NH_2$, and $-C(=O)CH_2CH_2NH_2$, and pharmaceutically acceptable salts thereof, in a pharmaceutically acceptable carrier.

A preferred type of cancer for treatment by pharmaceutical compositions including a compound of formula I is a p21-activated kinase (PAK)-dependent cancer. p21 activated kinases are members of a family of enzymes that serve as targets for the small GTP binding proteins CDC42 and Rac. Activation and/or overexpression of PAK has been identified as playing a role in various types of cancer, thereby resulting in a cancer that is dependent on PAK. In particular, breast cancer and thyroid cancer have been identified as being PAK-dependent cancers. Accordingly, in some embodiments, the method of the invention is directed specifically towards the treatment or prevention of breast cancer or thyroid cancer.

Cancer can be treated or prevented by regulating signaling pathways within the cancerous or potentially cancerous cells to prevent excessive growth or provide regulation of other aberrant processes within the cells. While not intending to be bound by theory, the compounds of the present invention can treat or prevent cancer by inhibiting one or more PAKs. As described in more detail in Example 1, the compounds of formula show increased activity and/or selectivity as PAK inhibitors.

The compounds of the invention can be used to provide prophylactic and/or therapeutic treatment. The compounds of the invention can, for example, be administered prophylactically to a subject in advance of the occurrence of cancer. Prophylactic (i.e., preventive) administration is effective to decrease the likelihood of the subsequent occurrence of cancer in the subject, or decrease the severity of cancer that subsequently occurs. Prophylactic treatment may be provided to a subject that is at elevated risk of developing cancer, such as a subject with a family history of cancer or exposure to high levels of carcinogens. The expression levels and/or activity of PAK represent two key determinants for cellular sensitivity to the compounds of formula I, and thus their levels may be useful as criteria for selecting patients to receive anticancer therapy using the compounds described herein.

Alternatively, the compounds of the invention can, for example, be administered therapeutically to a subject that is already afflicted by cancer. In one embodiment of therapeutic administration, administration of the compounds is effective to eliminate the cancer; in another embodiment, administration of the compounds is effective to decrease the severity of the cancer or lengthen the lifespan of the subject so afflicted. The subject is preferably a mammal, such as a domesticated farm animal (e.g., cow, horse, pig) or pet (e.g., dog, cat). More preferably, the subject is a human.

Another aspect of the invention provides a method of inhibiting a p21-activated kinase in a subject by administering an effective amount of a compound according to formula I:

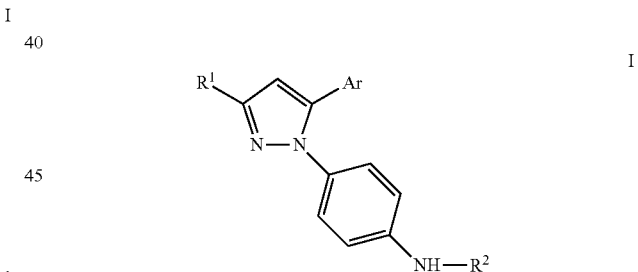

wherein Ar is a fused aryl group, $R^1$ is selected from alkyl and aryl amides, $CF_3$, and $CH_2OH$, and $R^2$ is selected from hydrogen, $-C(=O)CH_2NH_2$, and $-C(=O)CH_2CH_2NH_2$, and pharmaceutically acceptable salts thereof.

A number of p21-activated kinases are known to those skilled in the art. Examples of p21-activated kinases include PAK1, PAK2, PAK3, PAK4, PAK5, and PAK6. In some embodiments, a plurality of p21-activated kinases are inhibited, hence the term multikinase inhibitors. In other embodiments, the compound of formula I inhibits a particular kinase, either alone or in addition to other PAKs. For example, in one embodiment, the p21-activated kinase inhibited comprises PAK1. In further embodiments, the compounds of formula I show improved selectivity as kinase inhibitors. Improved selectivity, as used herein, means that the compounds show a higher level of ability to inhibit one type of kinases in comparison to one or more, or all other kinases. For example, in some embodiments, the compound does not substantially inhibit phosphoinositide-dependent kinase-1, which is not a PAK inhibitor.

Administration and Formulation of PAK Inhibitors

The present invention also provides pharmaceutical compositions that include compounds such as those defined by formula I as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compound, or by separately reacting a purified compound according to formula I with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds according to formula I together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The compounds of formula I can be administered as a single dose or in multiple doses. Useful dosages of the active agents can be determined by comparing their in vitro activity and their in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound according to formula I (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Figure 6:
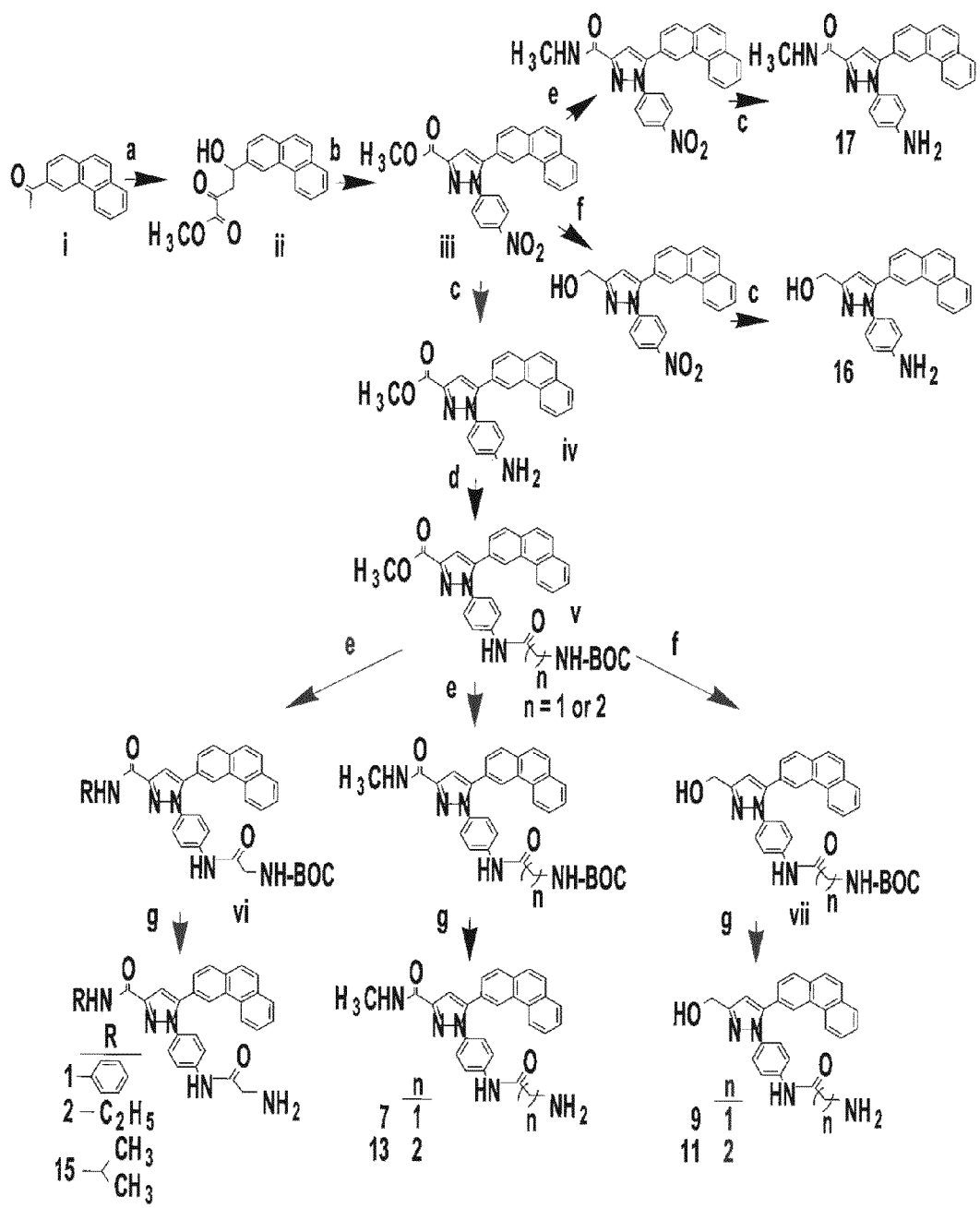
FIG. 6 (A-C) provides synthetic schemes for Series I-III of OSU-03012 derivatives, respectively. Reaction conditions.
Figure 6:
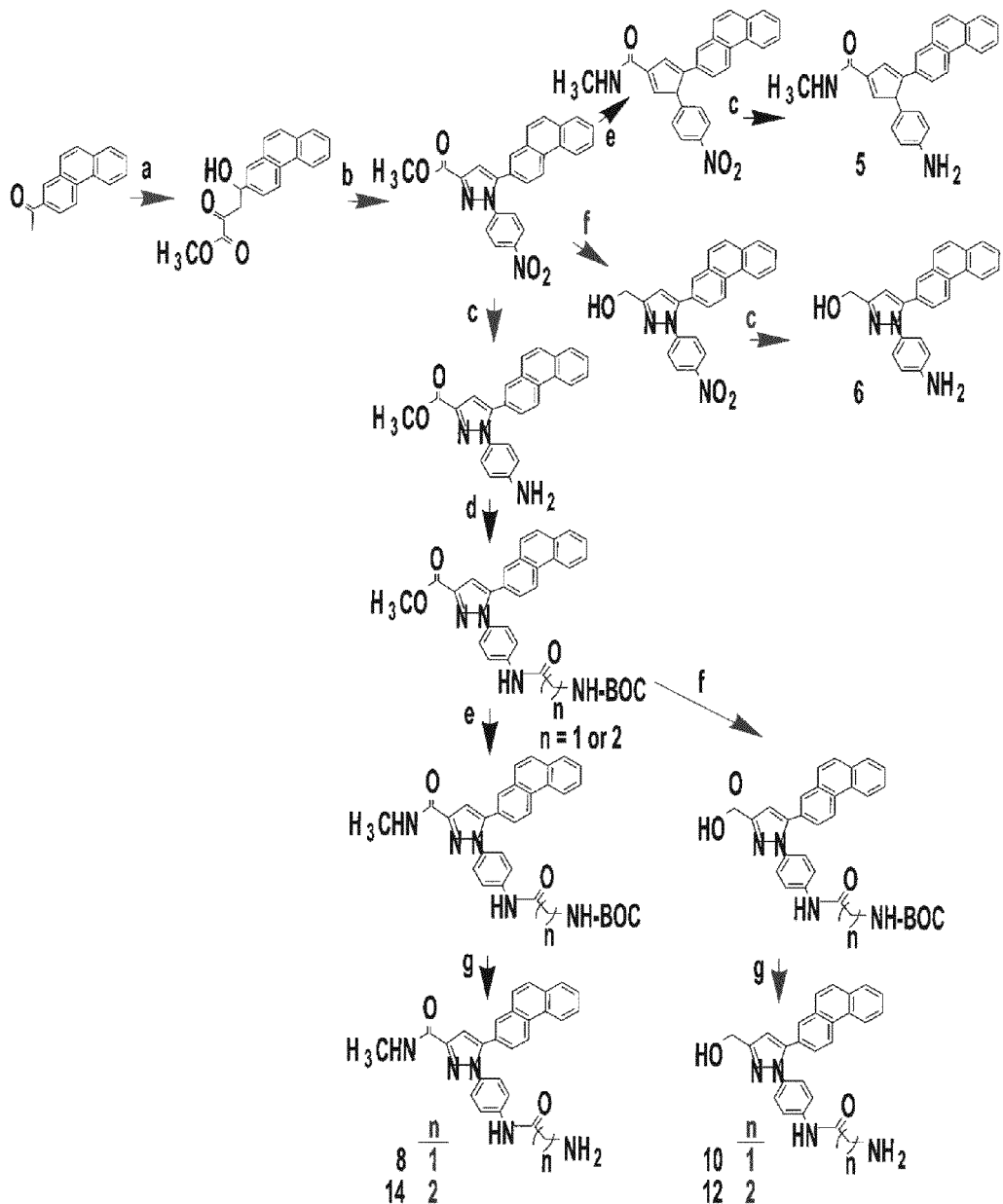
Figure 6:
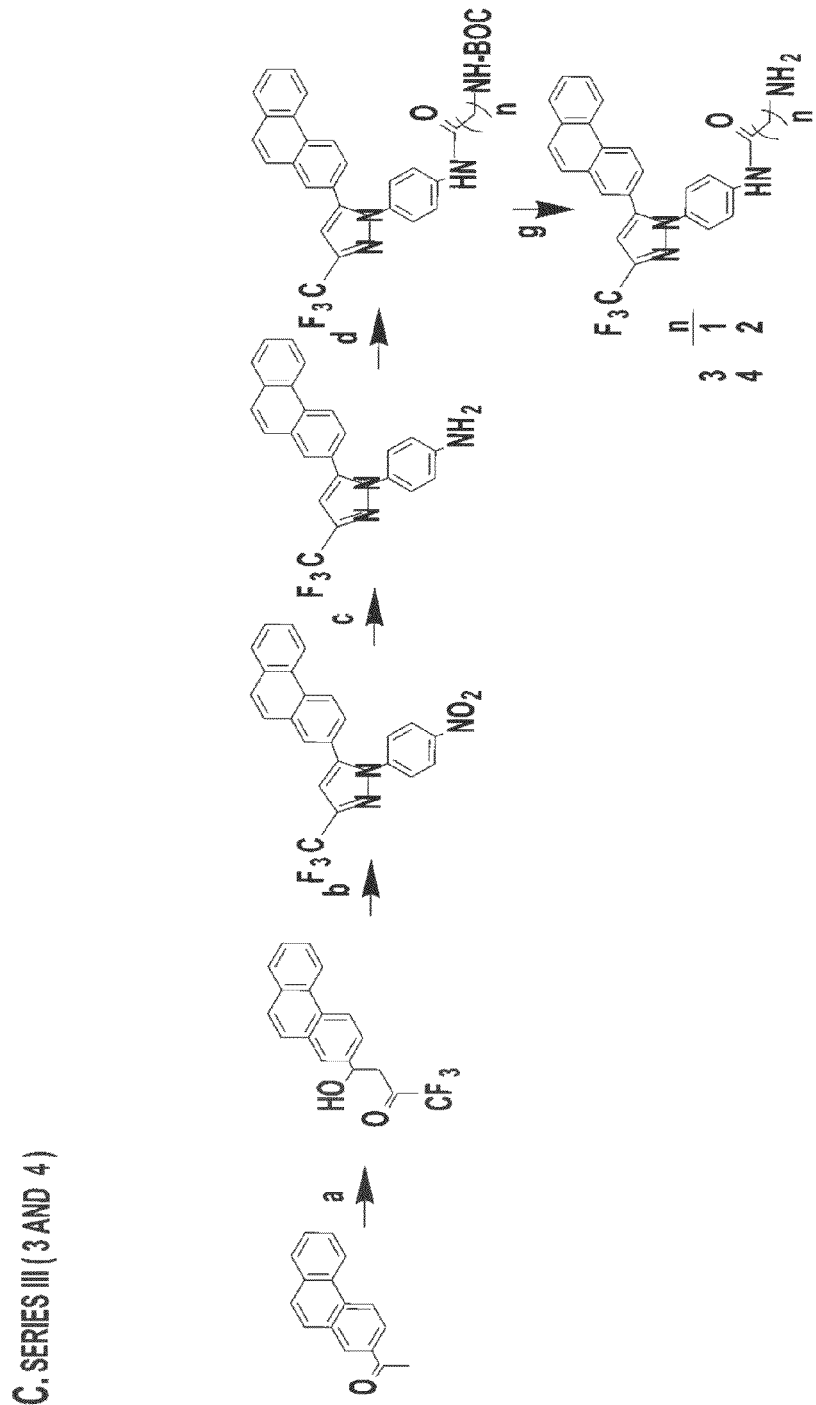

FIG. 6 illustrates a general synthetic scheme for preparing the compounds of the present invention. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Development of p21 Activated Kinase-Targeted Multikinase Inhibitors that Inhibit Thyroid Cancer Cell Migration PAKs are a family of downstream effectors of small GTPase cdc42 and rac that function as central regulators of cell motility and cytoskeletal rearrangement. Manser et al., Nature 367, 40-46 (1994). Six unique PAK isoforms have been cloned that are divided into two groups, PAKs 1-3 and PAKs 4-6, based on the sequence and functional characteristics. Bokoch, G M, Annual Review of Biochemistry, 340 72:743-781 (2003). As direct targets of Cdc42 and Rac, PAKs participate in a wide range of physiological processes beyond cell motility, including cell proliferation, apoptosis regulation, and in some systems, oncogenesis. Ong et al., Oncotarget 2:491-496 (2011). PAK activation and overexpression has been identified in a variety of malignancies. Dummler et al., Cancer Metastasis Rev 28:51-63 (2009). In thyroid cancer, we previously reported an increase in PAK1 expression, pPAK levels, and PAK-mediated phosphorylation of downstream effectors in the invasive fronts in aggressive papillary cancers. In further studies, Group 1 PAKs, and PAK1 in particular was essential for thyroid cancer cell motility in vitro. McCarty et al., Endocrine-related cancer 17: 989-999 (2010). In breast cancer, PAK activity correlates with the baseline invasiveness of human breast cancer cells and breast tumor grade. Adam et al., J.B.C., 275: 12041-12050 (2000). In addition, PAK1 is reported to contribute to the resistance of estrogen receptor (ER)—expressing breast cancers to tamoxifen by phosphorylating the Serine 305 in ER, thereby preventing its binding with estrogen. Holm et al., Natl Cancer Inst 98:671-680 (2006). A role for PAK in tumorigenesis in neurofibromatosis type 1 and 2 (NF1 and NF2) has also been characterized in detail (Yi et al., Cancer research 68:7932-7937 (2008)), and PAK isoforms are involved in Ras70 mediated tumorigenesis in several tissue types. Chow et al., Cancer research 72(22); 5966-75 (2012). Thus, it has been posited that PAK may be a relevant target for cancer therapy.

Over the past several years, there has been interest in developing compounds that inhibit the function of PAK isoforms or that down-regulate PAK isoform expression. Murray et al., PNAS, 107:9446-9451 (2010). We previously reported that OSU-03012, a multikinase inhibitor that inhibits PDK1 now in phase 1 clinical trials, also exhibits a previously unrecognized PAK inhibitory activity at low micromolar concentrations. Porchia et al., Mol Pharmacol 72:1124-1131 (2007) Moreover, in some cell lines, the inhibition of PAK occurred at lower concentrations than PDK1. Subsequent in vitro studies demonstrated that OSU-03012 directly targets PAK1 in an ATP-competitive manner and that the anti-migratory effect, but not the cell killing effect was rescued by overexpression of a constitutively active PAK 1. We embarked on the lead optimization of OSU-03012 to develop PAK inhibitors that do not also inhibit PDK1. In the present study, we report the development of two such compounds.

Chemistry

OSU-03012 was used as a platform to develop PAK1 inhibitors. As depicted in FIG. 1 and in greater detail in FIG. 6, three moieties of OSU-03012 were altered by using combinatorial strategies. The 2-phenanthrene in position A was modified to 3-phenanthrene to examine the conformational geometric effect on the activity, the B position $CF_3$ group was replaced with hydrogen-forming functional groups such as hydroxyl group and carboxamide groups; and the glycine at C position was either extended or shortened by being replaced with beta-Alanine or being cleaved off to examine the bulkiness effect. This combinatory strategy generated seventeen OSU-03012-derived compounds which were subject to biological evaluation.

Chemical reagents and organic solvents were purchased from Sigma-Aldrich (St. Louis, Mo.) unless otherwise mentioned. Nuclear magnetic resonance spectra ($^1$H NMR) were measured on a Bruker DPX 300 model spectrometer. Chemical shifts (δ) were reported in parts per million (ppm) relative to the TMS peak. Electrospray ionization mass spectrometry analyses were performed with a Micromass Q-T of II high-resolution electrospray mass spectrometer. The purity of all tested compounds are higher than 98% by 1H NMR and elemental analyses (Atlantic Microlab, Inc.; Norcross, Ga.). Flash column chromatography was performed using silica gel (230-400 mesh).

Cell Lines:

Human thyroid cancer BCPAP, TPC1, and FTC133 cell lines were the generous gifts of Drs. Rebecca Schweppe and Bryan Haugen (University of Colorado Denver) (Schweppe et al., The Journal of clinical endocrinology and metabolism 83:4331-4341 (2008)) with permission from the following originating laboratories: BCPAP—Dr. Fabien, Centre Hospitalier Lyon-Sud, France (Fabien et al., Cancer 73:2206-2212 (1994)); TPC1—Dr. Sato, Kanazawa University, Japan (Tanaka et al., Virology 161:62-411 (1987)); and FTC133—Dr. Goretzki, University of Leipzig, Germany (Goretzki et al., Recent Results Cancer Res 118:48-63 (1990)). The obtained cell lines were confirmed for identity by DNA fingerprinting. BCPAP was grown in RPMI 1640 medium (Life Technologies Co., Carlsbad, Calif.) while FTC133 and TPC1 were grown in DMEM (Life Technologies Co.), both supplemented with 10% fetal bovine serum (FBS) and NEAA unless as noted for experiments.

Cell Viability Analysis.

The effect of OSU-03012 and its derivatives on cell viability was assessed by using the 3-(4,5-dimethylthiazol-2-yl)-2, 5-diphenyl-2H-tetrazolium bromide (MTT) assay. Three replicates were performed in each individual experiment, and experiments were repeated at least three separate times. Cells were grown in 96-well plates for 24 hours and were exposed to various concentrations of drugs dissolved in DMSO (final concentration 0.1%) in RPMI 1640 or DMEM containing 1% FBS for 72 hours. 10 µL of 0.5 mg/ml MTT was added to each well and cells were incubated in $CO_2$ at 37° C. for 2 hours. Supernatants were removed from the wells, the reduced MTT dye was solubilized in 100 µL of solution C (12 ml of 1N HCl in 300 mL of isopropanol), and absorbance at 570 nm was determined on a microplate reader.

Kinase Assay:

Recombinant active PAK 1 (Calbiochem) was incubated with selected derivatives or 0.1% DMSO in the presence or absence of MBP (Sigma) in a 1× kinase buffer (Cell Signaling). The addition of [γ-32P]-ATP (2.5 µCi/reaction) (Perkin Elmer) started the reaction, which was incubated at 30° C. for 30 minutes. The reaction was terminated by the addition of EDTA. Results were obtained after visualization of $^{32}$P-labeled MBP after separation on 12% polyacrylamide gels and autoradiography. For the Lineweaver-Burk plot analysis, the ratio of radioactive ATP to nonradioactive ATP was not altered. The PAK1 kinase activities are the means of three independent experiments quantified using P81 phosphocellulose paper by a scintillation counter after three washes with 0.75% phosphoric acid.

Western Blot and Antibodies:

Protein isolation and Western blot were performed as previously described. Ringel et al., Cancer research 61:6105-6111 (2001). 25 µg of total cell lysates were loaded into 4-12% SDS-PAGE, electrophoresed, and transferred to nitrocellulose membranes for immunoblotting. Primary antibodies against Akt (#9272), phospho-Akt (Thr308) (#2965), p44/42 MAPK (Erk1/2) (#9107), phospho-p44/42 MAPK (Erk1/2) (Thr202/Tyr204) (#4377) and GAPDH (#2118) were obtained from Cell Signaling Technology (Danvers, Mass., USA). Antibody against Vimentin (V6630) and phospho-Ser55 Vimentin were from Sigma-Aldrich, Inc. (St. Louis, Mo.) and MBL Co. (Nagoya, Japan), respectively. Antibodies against total and phosphorylated S6 were from Cell Signaling Technology®.

Migration Assay:

Cells were grown in media containing 10% FBS. After 24 hours, the medium was aspirated, and media containing 1% FBS was added for 24 hours. The cells were trypsinized for 2 to 5 minutes, washed, and resuspended in media containing 1% FBS. The cell concentration was calculated by hemocytometer. Four hundred µl 1% FBS medium was added into 24-well plates, and a Boyden chamber (8 µm pore) was inserted into each well. Cells were added to each insert, and were allowed to attach in an incubator at 37° C. at 5% CO$_2$ for 2 hours. The cells were then exposed to various concentrations of drugs or control diluent for 3 hours. The inserts were switched to a new well containing media containing 10% FBS, and the chamber was incubated for 12 or 24 hours depending on the migration rate of the cell line. The cells on and under the Boyden chamber membrane were fixed with 3.7% formaldehyde containing 0.05% crystal violet for 15 min after washing cells with PBS. The chambers were washed with distilled water. The cells on the top (non-migrated) and bottom (migrated) sides of the membrane were collected by scraping the top and bottom of the chamber with a Q-tip, which was subsequently placed into a 1.5 ml tube. The remainder of the cells remained in the Boyden chamber. The Q-tips containing the scraped cells and the Boyden chamber containing the non-migrated cells were separately incubated in 80% methanol, shaken at 500 g for 30 minutes, and the extracted dye was measured at 570 nm. Migration was quantified as the ratio of the migrated cells over the total cells (non-migrated plus remaining cells). Experiments were performed in duplicate on at least three occasions.

Migration Rescue Experiments:

Myc-tagged constitutively activated (CA) PAK1 cDNAs was the generous gift of Dr. Jonathan Chernoff (Fox Chase Cancer Center, Philadelphia, Pa.). Sells et al., J Cell Biol 145:837-849 (1999). pRC/CMV and pcDNA3.1(+) vector were purchased from Life Technologies. BCPAP cells were grown in RPMI containing 10% FBS until 40-50% confluent. They were transfected with CAPAK1 cDNA or a vector control, washed with PBS, trypsinized with 0.05% Trypsin-EDTA 1× (Gibco) for 5-10 min, collected with 10% FBS RPMI, and centrifuged at 300 g for 5 min. Cells were resuspended with 0% FBS RPMI and counted using Countess™ (Invitrogen). Then a volume of 1×10$^5$ cells suspended in 300 µl of 0% FBS RPMI was placed into Boyden chamber inserts (8 µm pore). The inserts were placed into wells of a 24 well plate filled with 400 µl of 0% FBS RPMI. The plate was incubated at 37° C. 5% CO$_2$ for 1 hour. Then 30 µl (1 µM) of either compound 4 or 15 was added to the inserts and then incubated again for 1 hour. The inserts were transferred into different wells filled with 400 µl of 10% FBS RPMI. After incubation for 24 hours, the cells on either side of the insert membrane were fixed and quantified as above. Experiments were performed in triplicate on three occasions.

Statistical Analysis: Several of the experiments were conducted on different days; thus, linear mixed effects models were used to model any extra correlation of results within days (day-treatment random effects). We used saturated covariance structures to ensure that variances of test statistics were not underestimated. Holm's procedure was used to adjust for multiple comparisons or endpoints to strongly control type I error to a=0.05.

Results

Figure 2:
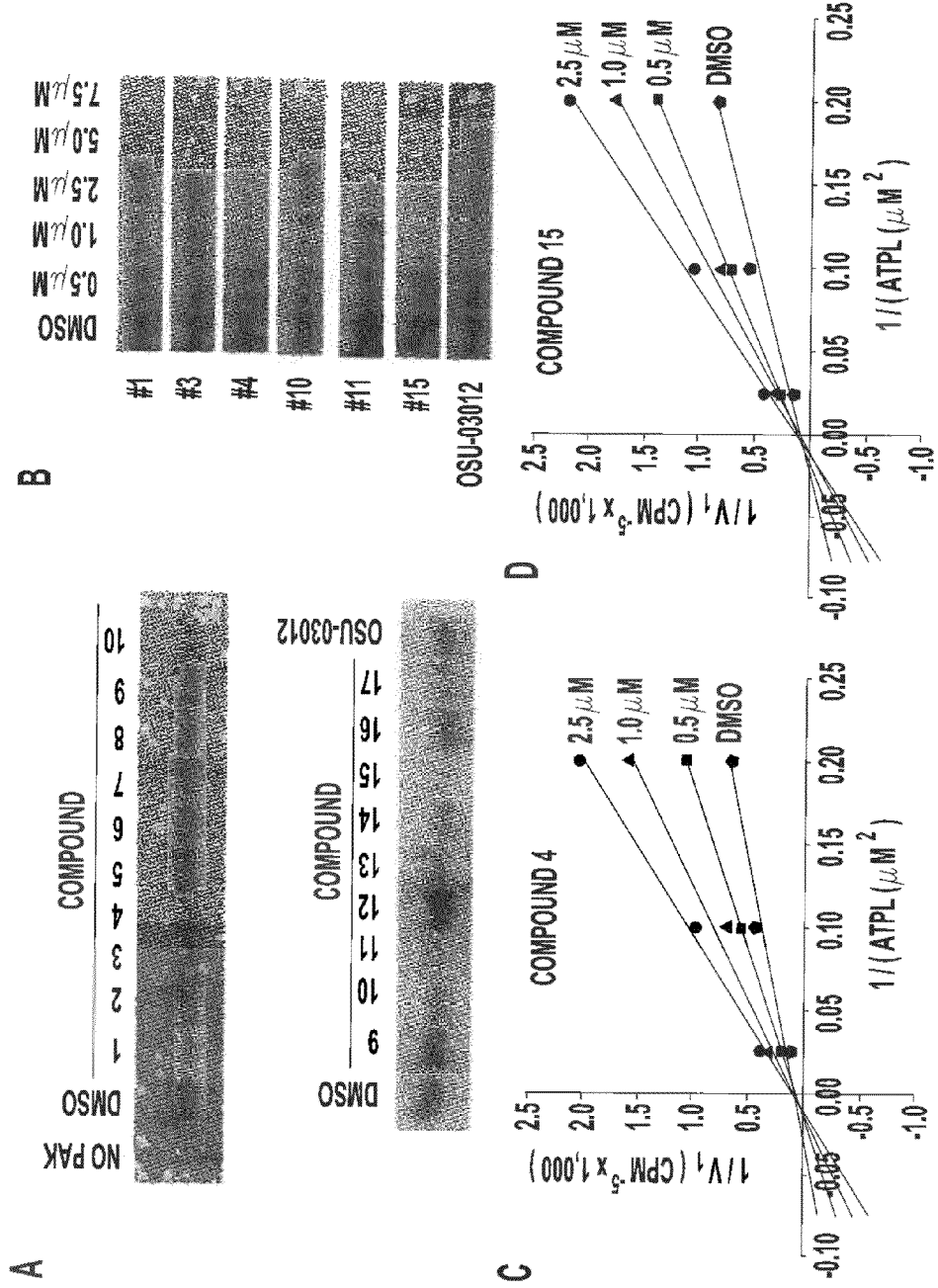
FIG. 2 provides graphs and images showing (A) In vitro kinase assay analysis of the PAK1 inhibitory activities of 17 compounds compared with OSU-03012; (B) Dose-response suppression of PAK1 activity by compounds 1, 3, 4, 10, 11, 15, and OSU-03012 at indicated concentrations; (C) ATP competition assay for PAK1 kinase. The activity of PAK1 was determined in the presence of varying concentrations of ATP (5-40 µM) at indicated concentrations of compounds 4 and 15. The plot shown is representative of three separate experiments performed in duplicate.

Screening of OSU-03012 Derivatives to Identify PAK1 Inhibitors. The 17 derivatives along with OSU-03012, each at 7.5 µM, were screened for their ability to inhibit PAK1 activity by in vitro PAK1 kinase assay. The dose was chosen (above the IC$_{50}$ of OSU-03012) to allow OSU-03012 to serve as a robust positive control. The PAK1 kinase assay was performed using recombinant active PAK1 with myelin basic protein as substrate in the presence of 2.5 µM ATP and 7.5 µM of respective inhibitors. The result of this initial screen demonstrated that among the compounds tested, six compounds, numbers 1, 3, 4, 10, 11, and 15, inhibited PAK1 kinase activity (FIG. 2A).

To further investigate these six compounds, dose-response studies on PAK1 activity were performed by using PAK1 kinase assay. All six compounds exhibited dose-related suppression of PAK1 activity (FIG. 2B), and at concentration greater than 5 µM, PAK1 activity was almost completely inhibited. Compounds 4 and 15 were more potent than the other compounds. Based on these results, we focused further efforts on these two compounds. We next questioned whether compounds 4 or 15 inhibited PAK1 in an ATP competitive manner as their parent compound OSU-03012. The ATP competition assays confirmed that both compounds competed with ATP binding to PAK1 as predicted based on the activity of OSU-03012 (FIGS. 2C and D).

Screening of OSU-03012 Derivatives for Cell Viability Effects

We assessed the ability of the compounds to reduce cell viability in vitro by MTT assay after 72 hours of continuous exposure. Results are shown in Table 1 and are depicted as the IC$_{50}$ vs. simultaneously performed DMSO control.

TABLE 1

Potencies of Compounds for Reducing Viability of BCPAP, FTC133 and TPC1 Cells Versus DMSO Control

| | IC$_{50}$$^a$ (µmol/L) | | |
|---|---|---|---|
| Compound | BCPAP | FTC133 | TPC1 |
| OSU-03012 | 2.93 ± 1.05 | 2.93 ± 1.87 | 2.80 ± 1.33 |
| 1 | 2.01 ± 0.59 | 4.78 ± 4.53 | 2.60 ± 0.81 |
| 2 | 2.67 ± 0.82 | 4.83 ± 4.47 | 1.81 ± 1.24 |
| 3 | 2.34 ± 0.27 | 5.32 ± 4.05 | 3.17 ± 1.29 |
| 4 | 2.07 ± 0.06 | 2.68 ± 2.08 | 1.68 ± 0.32 |

TABLE 1-continued

Potencies of Compounds for Reducing Viability of
BCPAP, FTC133 and TPC1 Cells Versus DMSO Control

| Compound | IC$_{50}$$^a$ (μmol/L) | | |
|---|---|---|---|
| | BCPAP | FTC133 | TPC1 |
| 5 | >10 | 5.03 ± 0.25 | >10 |
| 6 | >10 | >10 | >10 |
| 7 | 3.71 ± 1.82 | 4.53 ± 2.57 | 3.67 ± 1.52 |
| 8 | 2.90 ± 2.35 | 3.08 ± 1.63 | 4.67 ± 4.16 |
| 9 | 4.04 ± 1.38 | 4.75 ± 2.47 | 2.42 ± 0.13 |
| 10 | 6.53 ± 2.16 | 8.95 ± 0.57 | 7.39 ± 1.90 |
| 11 | 4.50 ± 1.04 | 3.94 ± 2.29 | 4.98 ± 1.94 |
| 12 | 3.76 ± 1.20 | 7.55 ± 2.19 | 5.83 ± 1.73 |
| 13 | 2.76 ± 1.56 | 4.95 ± 3.21 | 3.62 ± 0.42 |
| 14 | 3.32 ± 1.09 | 5.42 ± 1.56 | 5.98 ± 0.28 |
| 15 | 1.49 ± 0.68 | 3.37 ± 3.31 | 2.66 ± 1.05 |
| 16 | >10 | >10 | 4.32 ± 2.18 |
| 17 | >10 | >10 | 8.96 ± 1.17 |

$^a$The reported IC$_{50}$ values are concentrations at which BCPAP, FTC133 and TPC1 cell viability by MTT assays 50% of DMSO control after 72-hours of exposure. Data are presented as mean±standard deviation (n=3).

PAK and PDK1 Selectivity In Vivo

Figure 3:
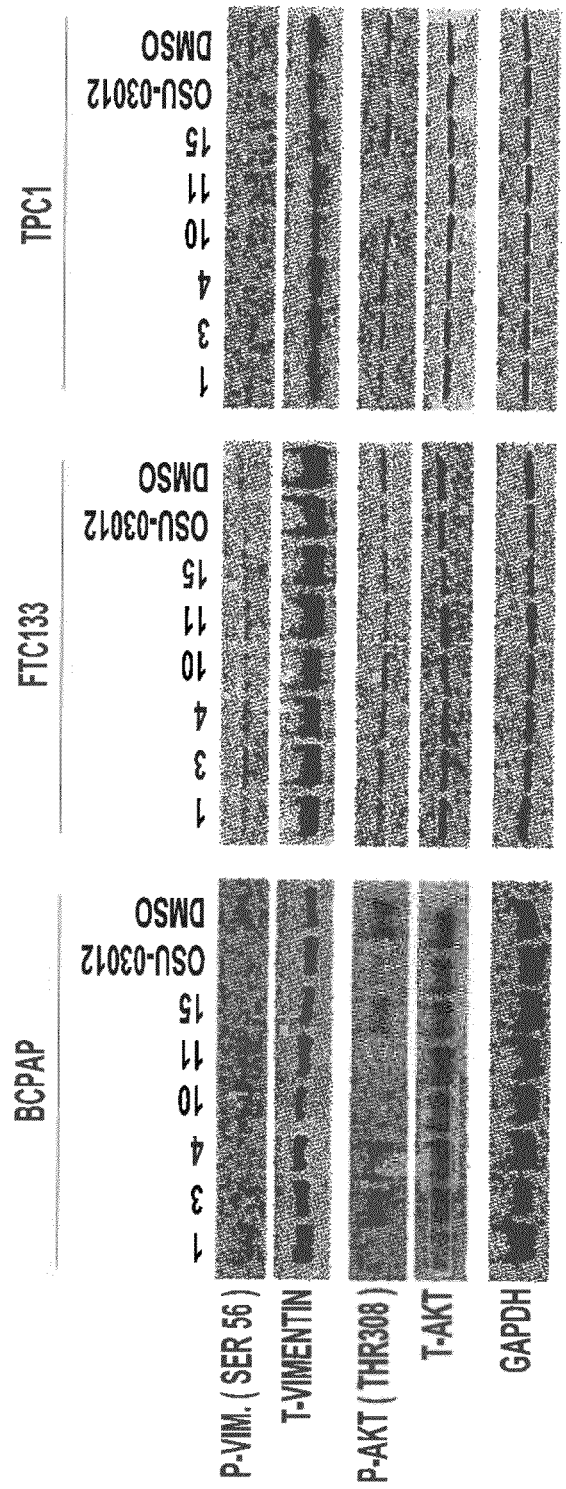
FIG. 3 provides a Western blot analysis of the effects of compounds with PAK inhibitory activities (1, 3, 4, 10, 11, and 15) versus OSU-03012 on PDK1 phosphorylation of Akt (Thr308) and PAK phosphorylation of Vimentin (Ser56) relative to that of DMSO after 6 h of treatment in BCPAP, FTC133 and TPC1 cells.

The ability of the compounds with in vitro anti-PAK1 activity was assessed for activity in vivo in thyroid cancer cells. In addition, because the compounds are based on the structure of a PDK1 inhibitor, PDK1 inhibitory activity was also assessed. Inhibitory activity in cells was estimated using Western blot with primary antibodies directed against kinase-specific phosphorylation sites; serine 56 of vimentin for PAK and threonine 308 of Akt for PDK1. BCPAP, TPC1, and FTC133 thyroid cancer cells were utilized. BCPAP and TPC1 are derived from PTC and have BRAF V600E and RET/PTC1 rearrangements, respectively. FTC133 is derived from a follicular thyroid cancer with an inactivating mutation of PTEN. Similar to the kinase screening assay, cells were treated with the six compounds or OSU-03012 at 7.5 μM concentration or with DMSO vehicle alone. The results are shown in FIG. 3. The results were not entirely consistent across the three cell lines presumably related to mutation status or other factors. OSU-03012 inhibited both PDK1 and PAK-mediated phosphorylation of targets as predicted. Only compounds 4 and 15 inhibited PAK without altering PDK1 activity in at least two cell lines. Compound 11 did not significantly alter PAK phosphorylation of vimentin but did markedly inhibit PDK1 phosphorylation of Akt suggesting specificity for PDK1.

Figure 4:
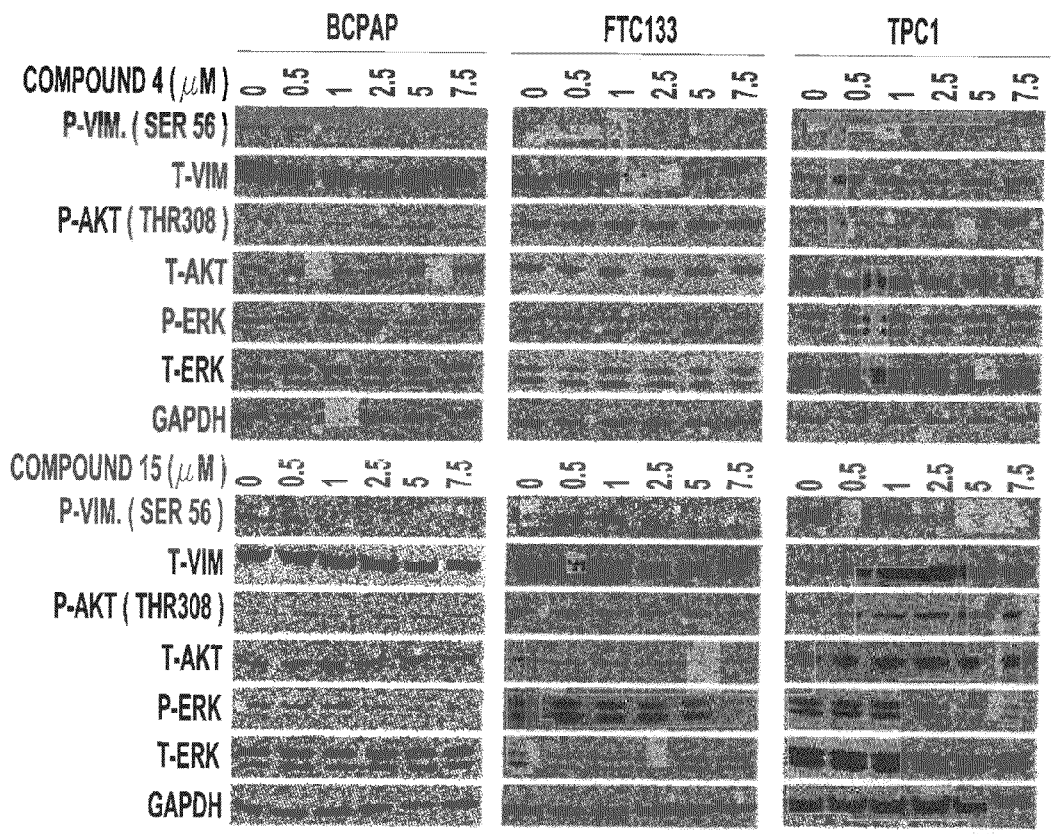
FIG. 4 provides (A) a Western blot analysis of the dose-dependent effect of compounds 4 and 15 on the phosphorylation of Vimentin, Akt and ERK in BCPAP, FTC133 and TCP1 cells after 6 hours of drug treatment and (B) a Western blot analysis of the suppressive effects of compounds 4 and 15 on S6 phosphorylation.
Figure 4:
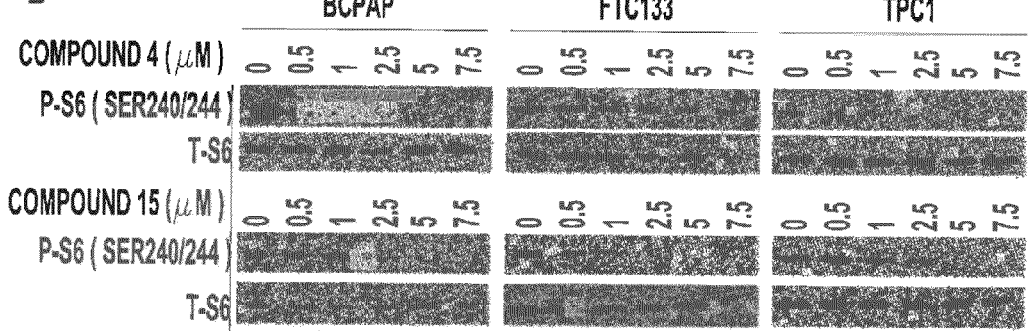

The dose-dependency of compounds 4 and 15 was next assessed (FIG. 4). Consistent with the kinase assay and initial cell line results, both compounds inhibited PAK1 in a dose dependent manner and PDK-mediated Akt phosphorylation was not reduced (FIG. 4A). Due to the important role that ERK activation plays in thyroid cancer, and its signaling activation by thyroid oncogenes, the effects of the compounds on ERK phosphorylation was also assessed. Compound 15 inhibited ERK phosphorylation at 2.5 μM in the BCPAP cells with a BRAF V600E mutation and at higher concentrations in the other two cell lines. In contrast, compound 4 had no demonstrable effects on ERK phosphorylation (FIG. 4A). Finally, based on the multikinase assay result that demonstrated inhibition of p70S6 kinase activity (see below and Table 2), we also assessed for an effect on 56 phosphorylation and demonstrated that compound 15 inhibited 56 phosphorylation in all cell lines while compound 4 inhibited this phosphorylation in BCPAP and TPC1, but not in the FTC 133 cells (FIG. 4B).

TABLE 2

The inhibition of kinase in vitro activities by Compounds 4 and 15

| | Compound 4 (% activity vs. DMSO) | Compound 15 (% activity vs. DMSO) | | Compound 4 (% activity vs. DMSO) | Compound 15 (% activity vs. DMSO) |
|---|---|---|---|---|---|
| CaMKI | 65 | 68 | PAK2 | 70 | 81 |
| CDK1/cyclinB | 83 | 95 | PAK4 | 101 | 105 |
| CDK5/p25 | 113 | 93 | PAK3 | 211 | 99 |
| CHK1 | 82 | 89 | PAK5 | 114 | 104 |
| C-RAF | 104 | 108 | PAK6 | 81 | 101 |
| EGFR | 99 | 100 | PKA | 110 | 119 |
| FAK | 87 | 96 | PKBα | 103 | 99 |
| FGFR2 | 92 | 99 | PKBβ | 76 | 84 |
| GSK3α | 133 | 118 | PKBγ | 33 | 56 |
| GSK3β | 170 | 137 | PKCα | 92 | 92 |
| IGF-1R, activated | 97 | 83 | PKCδ | 85 | 110 |
| JAK2 | 152 | 139 | Ret | 97 | 76 |
| LIMK1 | 130 | 117 | ROCK-I | 93 | 95 |
| MEK1 | 106 | 101 | ROCK-II | 79 | 96 |
| Met | 89 | 77 | SGK | 27 | 64 |
| p70S6K | 28 | 38 | Src(T341M) | 105 | 94 |

$^a$ 32 kinases were selected from different kinase superfamilies. Both compounds were tested using 5 μM concentrations. The values are average of triplicate with variations of less than 15%.

Compounds 4 and 15 are Multikinase Inhibitors

To further probe the selectivity of the compounds 4 and 15, they were subjected for kinase profiling service for screening against a panel of other kinases selected based on the kinase tree at 5 μM concentration, at or above the IC$_{50}$ for the two compounds versus PAK in both in vitro and cell-based assays. Of a panel of 32 kinases tested, three kinases, SGK, p70S6K and PKBγ displayed greater than 50% inhibition by 5 μM compound 4; while only one kinase p70S6K was inhibited by greater than 50% by compound 15 (Table 1). The two compounds also did not have activity versus other PAK kinases on this assay. PAK1 was not available for testing using this system thus it was not possible to compare directly in this assay system.

Constitutively Active PAK Partially Rescues Migration Inhibited by Compounds 4 and 15

Figure 5:
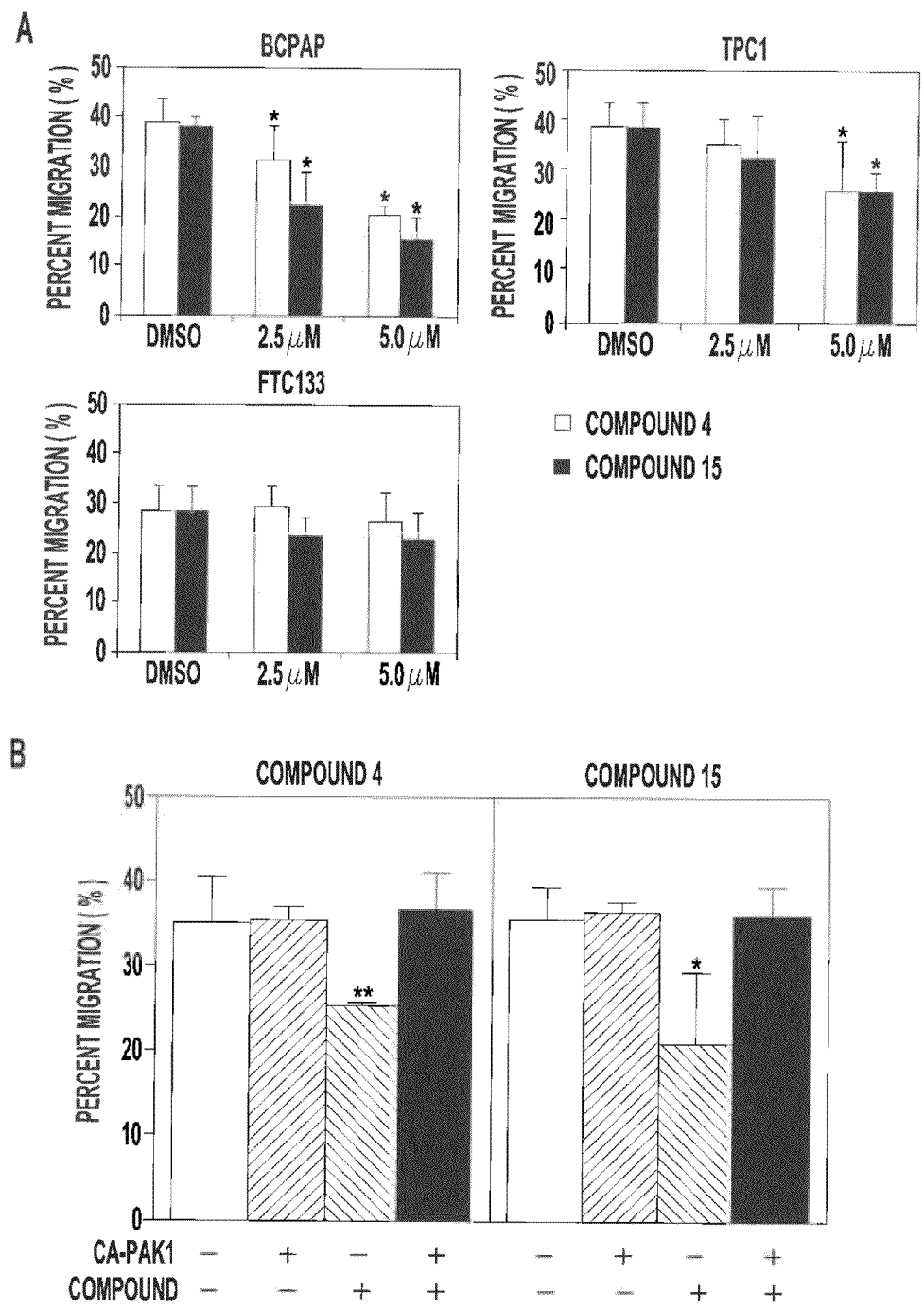
FIG. 5 provides graphs showing the inhibition effect of compounds 4 and 15 on cell migration after 12 or 24 hours of treatment. (A) Compounds 4 and 15 inhibited migration of BCPAP cells at 2.5 µM and 5.0 µM concentrations (*P<0.05 versus DMSO) after 12 hours treatment; both compounds inhibited migration of TPC1 cells at 5 µM (*P<0.05 versus DMSO) after 24 hours of treatment; neither compound significantly inhibited migration of FTC133 cells at either 2.5 µM or 5.0 µM concentrations after 12 hours of treatment. (B) Transfection of BCPAP cells with a constitutively activated PAK1 cDNA rescues the inhibition of migration of both compounds (P<0.05). Rescue experiments for each compound were performed on three separate occasions.

Because the compounds are multikinase inhibitors, we next sought to determine if PAK1 inhibition was responsible for some of the biological effects of the compounds. We have previously demonstrated a critical role for PAK isoforms in thyroid cancer cell motility using several molecular inhibitors and that a constitutively active form of PAK1 rescued the effect of OSU-03012 on cell migration. Thus, we performed migration assays to assess the effects of compounds 4 and 15 on the cell motility of BCPAP, FTC133 and TPC1 cells using Boyden chambers. Preliminary experiments were performed to determine doses of each compound that did not reduce cell viability over 24 hours. As shown in FIG. 5A, BCPAP cells motility was inhibited by both compounds at 2.5 μM and 5.0 μM concentrations, respectively. Both compounds also decreased cell motility in TPC1 cells, although the effect was less pronounced. In contrast, FTC133 cell motility was not inhibited by either compound. The reason for this difference is not certain. To confirm that PAK inhibition was responsible for the reduction in migration, BCPAP cells were transfected with a constitutively activated PAK1 cDNA, and migration experiments were performed in the presence or absence of compounds. Expression of the constitutively activated PAK1 rescued the anti-migratory effects of compounds 4 and 15 (FIG. 5B).

Discussion:

PAK1 is overexpressed in the invasive fronts of thyroid cancer and is functionally important in regulating thyroid cancer cell motility. This study builds on our prior identification of anti-PAK kinase activity of OSU-03012, a competitive ATP-binding compound that also inhibits other kinases, including PDK1. Seventeen second-generation compounds were developed with the goal of maintaining or enhancing PAK inhibition while limiting or abolishing the anti-PDK1 effect. Six compounds were identified that inhibited PAK activity in vitro. SAR analysis indicates that there is a conformational geometry effect on their activity to inhibit PAK1. For example, compound 3 demonstrated slightly more potent activity based on in vitro kinase assay than OSU-03012 and in structure they are identical except the conformation of the phenanthrene, suggesting a different binding mode of these two isoforms. This premise is further supported by other pairs of isoforms: for example, compound 10, which bears the same phenanthrene moiety as OSU-03012, demonstrated more potent activity in inhibiting PAK1 activity while its isoform compound 9 did not show any improvement in PAK1 inhibitory activity. This may suggest that the binding mode of OSU-03012, and compound 10, favor a hydrophilic group at site B (FIG. 1), while a hydrophobic group is able to increase the potency of the derivatives whose binding mode is similar to that of compounds 3 and 9. This hypothesis is further supported by the relative enhancement in activity of compound 15 vs compounds 2 and 7. These compounds all contain the 3-phenanthrene ring, suggesting they adopt the $2^{nd}$ conformation, paralleling the bulkiness of the groups at B position. In summary, the preference of a functional group at B position appears to correlate with cooperativity with phenanthrene conformation.

A bulky group at position C was observed to be associated with higher PAK1 inhibitory potency by comparing the activity of compounds with otherwise similar structures. Specifically, compounds 4, 11, 13 and 14 were more potent than compounds 9, 3, 7, and 8, respectively. In each of these compound pairs the first compound contains a bulkier beta-alanine versus a glycine. Moreover, compounds 5, 6, 16, and 17 that do not contain an amino acid residue at that site did not show any activity. Taken together, the findings support the importance of a bulky group at C position regardless of the binding mode for anti-PAK activity.

Among all the derivatives examined, compounds 4 and 15 had comparable PAK1 inhibitory activity to OSU-03012 but did not block PDK1-mediated Akt phosphorylation on the Western blot in vivo assay. This relative selectivity may result from the larger bulkiness of compounds 4 and 15, which would be predicted to prevent binding to the ATP pocket of PDK1; on the other hand, the open ATP-binding site of PAK1 is predicted to accommodate the bulky sizes of compounds 4 and 15. This is consistent with previous reports that more selective inhibition of PAK is achieved by enlarging the size of lead compounds. Maksimoska et al., JACS, 130:15764-15765 (2008); Nheu et al., Cancer journal 8:328-336 (2002).

It is interesting to note that the results of the in vitro kinase assay did not completely match the cell line Western blot data. There are several potential reasons for this, including the likelihood that PAK folding and protein-protein interactions are important determinants of compound activity that are not assessed in the in vitro assay. In addition, there are other mechanisms of resistance in cells such as difficulty in compounds entering cells through the cell membrane, inactivating metabolism of compounds, enhanced export of compounds and others that may account for the differences.

The ability of the compounds to reduce the viability of BCPAP, FTC133 and TPC1 thyroid cancer cells were assessed and are shown in Table 1. Several of the compounds did not reduce cell viability in the cell lines. In contrast, compounds 4 and 15 were amongst the most active for each of the cell lines. The correlation with the anti-PAK activity was not always noted; however, PAK1 inhibition was not responsible for the cell death effect of the parent OSU-03012 compound. In light of the cell viability suppression, a dose-response study of the effect of these two compounds on ERK phosphorylation was also performed due its central role in mediating thyroid cancer cell proliferation and apoptosis. Interestingly, compound 15 inhibited ERK phosphorylation while compound 4 did not, even at high concentrations. The mechanism for the inhibition of ERK is not certain as compound 15 did not inhibit either cRAF or MEK on the multi-kinase screen. Further analysis of this inhibitory effect is ongoing. Because of the important role of PAK on cell migration and our prior data suggesting that expression of the constitutively activated PAK rescued the effect of OSU-03012 on migration, we performed similar experiments. Based on initial studies, it appeared that the BCPAP cells were most sensitive to the anti-migratory effects of the two compounds. Thus, this cell line was selected for rescue experiments, and as demonstrated in FIG. 5, there was a rescue effect on this property. These data suggest that PAK inhibition is responsible, at least in part, for the anti-migration effect of compounds 4 and 15. Finally, based on the compound screen we also confirmed that both compounds 4 and 15 inhibit phosphorylation of S6 consistent with the findings from the kinase profiling assay. Thus, these compounds should be recognized as multikinase inhibitors that included anti-PAK1 activity but are not PAK-specific.

In summary, we have developed several new derivatives of OSU-03012 that have maintained effects on PAK1 but do not appear to inhibit PDK1 function in vivo. The compounds are multikinase inhibitors that demonstrate some degree of unique specificity. The development of compounds 4 and 15 provide a proof of concept that enlarging the size of the lead compound contributes to the development of PAK inhibitors and also demonstrate that further modification and structure-function studies are needed to devise more potent and selective inhibitors of this important kinase target.

Example 2

Compound Synthesis

Chemical reagents and organic solvents were purchased from Sigma-Aldrich (St. Louis, Mo.) unless otherwise mentioned. Nuclear magnetic resonance spectra (1H NMR) were measured on a Bruker DPX 300 model spectrometer. Chemical shifts (δ) were reported in parts per million (ppm) relative to the TMS peak. Electrospray ionization mass spectrometry analyses were performed with a Micromass Q-T of II high-resolution electrospray mass spectrometer. Elemental analyses were performed by Atlantic Microlab, Inc. (Norcross, Ga.) and were reported to be within 0.4% of calculated values. Flash column chromatography was performed using silica gel (230-400 mesh). The three series of compounds: Series I (1, 2, 7, 9, 11, and 13-17), II (5, 6, 8, 10, 12, and 14), III (3 and 4), were synthesized according to the general schemes described in FIG. 6A-C, respectively, which is illustrated by the synthesis of compounds 15 and 9 as an example.

1-(4-(2-Aminoacetamido) phenyl)-N-isopropyl-5-(phenanthren-3-yl)-1H-pyrazole-3-carboxamide (15) Step a. To the mixture of 1-(phenanthren-3-yl)ethanone (1; 6.6 g, 30 mmol) and diethyl oxalate (2 ml) in MeOH (100 mL) was added sodium hydride (2.9 g, 120 mmol) portion-wise within 10 min. The reaction mixture was stirred at room temperature for 4 h, cooled down to 0° C. and acidified with 2N HCl. The precipitate was collected, washed with cold ethanol and dried to yield (Z)-methyl 4-hydroxy-2-oxo-4-(phenanthren-3-yl)but-3-enoate (1) as yellow crystal (7.3 g, 80%). It was used for the next step without further purification. $_1$H-NMR (300 MHz, DMSO-$d_6$) δ 9.47 (s, 1H), 9.09 (d, J=7.8 Hz, 1H), 8.26 (d, J=9.0 Hz, 1H), 8.15 (d, J=9.0 Hz, 1H), 8.06-8.01 (m, 2H), 7.94 (d, J=7.8 Hz, 1H), 7.80-7.69 (m, 2H), 7.51 (s, 1H), 3.90 (s, 3H).

Step b. A suspension of the 1,3-diketone ii (2.6 g, 8.2 mmol) in absolute ethyl alcohol (200 ml) was treated with concentrated HCl (1 ml) and 4-nitrophenylhydrazine (1.70 g, 0.9 mmol). The reaction mixture was left for overnight. The reaction was monitored by using thin layer chromatography. After the reaction was complete, the precipitate was collected by filtration, washed with ethanol and dried to give methyl 1-(4-nitrophenyl)-5-(phenanthren-3-yl)-1Hpyrazole-3-carboxylate (iii) as yellow solid (2.0 g, 60%). $_1$H-NMR (300 MHz, DMSO-$d_6$) δ 8.94 (s, 1H), 8.75-8.72 (m, 1H), 8.27 (d, J=9.0 Hz, 2H), 8.01-7.82 (m, 4H), 7.67-7.64 (m, 4H), 7.46 (s, 1H), 7.40 (d, J=8.1 Hz, 1H), 3.91 (s, 3H).

Step c. A stirred mixture of compound iii (0.78 g, 1.84 mmol), hydrazine (2 ml, 11 mmol) and Pd/C (60 mg) in ethanol (20 ml) and THF (20 ml) was refluxed for 5 h. The reaction mixture was allowed to cool down and filtered through Celite, the filtrate was evaporated to dryness. The solid residue methyl 1-(4-aminophenyl)-5-(phenanthren-3-yl)-1H-pyrazole-3-carboxylate (Iv) (650 mg, 90%) was collected and used for next step without further purification. $^1$H NMR (300 MHz, DMSO-$d_6$) •• δ 8.62 (s, 1H), 8.44-8.42 (m, 1H), 7.91-7.88 (m, 1H), 7.83-7.73 (m, 2H), 7.71 (s, 1H), 7.67-7.58 (m, 2H), 7.42-7.39 (m, 1H), 7.23 (s, 1H), 7.18 (d, J=8.61 Hz, 2H), 6.62 (d, J=8.67 Hz, 2H), 4.00 (s, 3H).

Step d. To a solution of compound 1v (200 mg, 0.5 mmol) and Boc-glycine (100 mg, 0.57 mmol) in dry THF (20 ml) was added EDC (100 mg, 0.55 mmol) at once. The mixture was stirred for overnight under $N_2$. The reaction was monitored by using TLC. After starting material disappeared, the reaction was quenched with water, extracted with ethyl acetate, washed with brine, dried over anhydrous sodium sulfate and concentrated. Purification using column chromatography (EA/Hexane=1:2) afforded methyl 1-(4-(2-((tert-butoxycarbonyl)-amino)acetamido)phenyl)-5-(phenanthren-3-yl)-1H-pyrazole-3-carboxylate (v; 178 mg, 65%). $^1$H NMR (300 MHz, DMSO-$d_6$ •• δ ppm 10.13 (s, 1H), 8.80 (s, 1H), 8.63 (m, 1H), 7.99-7.77 (m, 5H), 7.68-7.62 (m, 4H), 7.42 (s, 1H), 7.36-7.33 (m, 2H), 7.06 (s, 1H), 4.00 (s, 3H), 3.79 (s, 2H), 1.47 (s, 9H).

Step e. To a solution of isopropylamine (33% in methanol) (5 mL) was added compound v (200 mg, 36 mmol). The mixture was heated at 100° C. in sealed tube for overnight. The reaction was monitored by TCL. After completion, the solvent was removed under reduced pressure to yield desired product tert-butyl (2-((4-(3-(isopropylcarbamoyl)-5-(phenanthren-3-yl)-1H-pyrazol-1-yl)phenyl)amino)-2-oxoethyl)carbamate (vi; 180 mg, 91%). $^1$H NMR (300 MHz, DMSO-$d_6$ • δ10.13 (s, 1H), 8.78 (s, 1H), 8.62-8.60 (m, 1H), 8.06-7.82 (m, 5H), 7.67-7.64 (m, 4H), 7.40-7.37 (m, 3H), 7.27 (s, 1H), 7.08 (s, 1H), 4.16-4.14 (m, 1H), 3.88-3.79 (m, 2H), 1.47 (s, 9H), 1.19 (d, J=6.07 Hz, 6H).

Step g. The mixture of compound vi (60 mg, 0.11 mmol) in HCl solution (3N in methanol) (5 mL) was stirred for 3 h. 10% sodium carbonate was then added. The stirring was continued for another 3 h. The reaction mixture was extracted with ethyl acetate three times, and the combined organic layers were washed with brine, dried over anhydrous sodium sulfate and concentrated. Purification on column chromatography provides 15 as white solid (28 mg, 60%). $^1$H NMR (300 MHz, DMSO-$d_6$ •• δ 8.77 (s, 1H), 8.62 (m, 1H), 8.06-7.97 (m, 2H), 7.93-7.79 (m, 3H), 7.72-7.63 (m, 4H), 7.42-7.37 (m, 3H), 7.26 (s, 1H), 4.21-4.07 (m, 1H), 3.83-3.70 (m, 2H), 1.19 (d, J=6.07 Hz, 6H). HRMS calcd for $C_{33}H_{27}N_5O_2$ $(M+Na)^+$ 500.2026. found 500.2087. Anal. ($C_{33}H_{27}N_5O_2$) C, H, N.

2-Amino-N-(4-(3-(hydroxymethyl)-5-(phenanthren-3-yl)-1H-pyrazol-1-yl)phenyl)-acetamide (9). Step f. To a suspension of LiAlH$_4$ (300 mg) in dry THF at 0° C. was added dropwise a solution of compound v (140 mg, 0.25 mmol) in THF (5 ml). The reaction mixture was stirred for 1 h and quenched with saturated sodium sulfate solution. The resulting mixture was filtered through Celite and concentrated. The residue was applied to column chromatography to afford tert-butyl (2-((4-(3-(hydroxymethyl)-5-(phenanthren-3-yl)-1H-pyrazol-1-yl)phenyl)-amino)-2-oxoethyl)carbamate (vii; 78 mg, 60%). 1H NMR (300 MHz, DMSO-d6 • δ 8.54 (m, 1H), 8.35-8.23 (m, 1H), 7.90-7.82 (m, 2H), 7.80-7.69 (m, 2H), 7.60-7.53 (m, 3H), 7.12 (d, J=9 Hz, 2H), 6.80 (s, 1H), 6.67 (d, J=9 Hz, 2H), 4.71 (s, 2H), 3.79 (s, 2H), 1.47 (s, 9H). Compound vii underwent step g to furnish 9. 1H NMR (300 MHz, DMSO-d6 •• δ 8.77-8.66 (m, 1H), 8.64-8.54 (m, 1H), 8.03-7.75 (m, 4H), 7.71-7.55 (m, 4H), 7.44-7.34 (m, 1H), 7.34-7.27 (m, 2H), 6.89-6.79 (m, 1H), 4.56 (s, 2H), 3.79 (s, 2H). HRMS calcd for $C_{26}H_{22}N_4O_2$ $(M+H)^+$ 445.1640. found $(M+H)^+$ 445.1647.

1-(4-(2-Aminoacetamido)phenyl)-N-benzyl-5-(phenanthren-3-yl)-1H-pyrazole-3-carboxamide (1). $^1$H NMR (300 MHz, DMSO-$d_6$ •• δ 9.01-8.88 (m, 1H), 8.85-8.75 (m, 1H), 8.72-8.58 (m, 1H), 8.07-7.76 (m, 4H), 7.76-7.60 (m, 3H), 7.49-7.28 (m, 9H), 4.58 (s, 2H), 3.91 (s, 2H). HRMS calcd for $C_{33}H_{27}N_5O_2$ $(M+Na)^+$ 548.2062. found 548.2081.

1-(4-(2-aminoacetamido)phenyl)-N-ethyl-5-(phenanthren-3-yl)-1H-pyrazole-3-carboxamide (2). $^1$H NMR (300 MHz, DMSO-$d_6$ •• δ8.83-8.72 (m, 1H), 8.69-8.57 (m, 1H), 8.44-8.30 (m, 1H), 8.03-7.76 (m, 4H), 7.66-7.60 (m, 3H), 7.42-7.35 (m, 3H), 7.30 (s, 1H), 3.85-3.70 (m, 2H), 3.53-3.43 (m, 2H), 1.13 (t, J=7.21 Hz, 3H). HRMS calcd for $C_{33}H_{27}N_5O_2$ $(M+Na)^+$ 486.1906. found 486.1924.

2-Amino-N-(4-(5-(phenanthren-3-yl)-3-(trifluoromethyl)-1H-pyrazol-1-yl)phenyl)-acetamide (3). $^1$H NMR (300 MHz, DMSO-$d_6$) δ 8.84 (m, 1H), 8.66-8.63 (m, 1H), 8.22-8.21 (m, 3H), 7.99-7.80 (m, 3H), 7.70-7.68 (m, 3H), 7.44-7.25 (m, 3H), 3.86-3.69 (m, 2H). HRMS calcd for $C_{33}H_{27}N_5O_2$ (M+Na)$^+$ 483.1409. found 483.1404.

3-amino-N-(4-(5-(phenanthren-3-yl)-3-(trifluoromethyl)-1H-pyrazol-1-yl)phenyl)-propanamide (4). $^1$H NMR (300 MHz, DMSO-$d_6$) δ 8.76 (s, 1H), 8.60-8.58 (m, 1H), 7.96-7.78 (m, 6H), 7.69-7.60 (m, 3H), 7.51-7.31 (m, 3H), 2.97 (t, J=6.0 Hz, 2H), 2.67 (t, J=6.0 Hz, 2H). HRMS calcd for $C_{33}H_{27}N_5O_2$ (M+Na)$^+$ 497.1565. found 497.1564. Anal. ($C_{33}H_{27}N_5O_2$) C, H, N.

1-(4-Aminophenyl)-N-methyl-5-(phenanthren-2-yl)-1H-pyrazole-3-carboxamide (5). $^1$H NMR (300 MHz, DMSO-$d_6$) δ 8.78 (t, J=7.80 Hz, 2H), 8.12-7.95 (m, 2H), 7.82 (m, 2H), 7.74-7.60 (m, 2H), 7.50-7.35 (m, 3H), 7.25 (d, J=8.20 Hz, 2H), 7.17 (s, 1H), 2.79 (d, J=4.49 Hz, 3H). HRMS calcd for $C_2H_{22}N_4O$ (M+H)$^+$ 415.1535. found (M+H)$_+$ 415.1527.

1-(4-Aminophenyl)-5-(phenanthren-2-yl)-1H-pyrazol-3-yl) methanol (6). $^1$H NMR (300 MHz, DMSO-$d_6$) δ 8.93-8.65 (m, 2H), 8.00 (s, 2H), 7.94-7.75 (m, 2H), 7.73-7.60 (m, 2H), 7.35 (d, J=8.64 Hz, 5H), 6.78 (s, 1H), 4.55 (s, 2H). HRMS calcd for $C_{24}H_{21}N_3O$ (M+H)$^+$ 388.1426. found (M+H)$^+$ 388.1427.

1-(4-(2-aminoacetamido)phenyl)-N-methyl-5-(phenanthren-3-yl)-1H-pyrazole-3-carboxamide (7). $^1$H NMR (300 MHz, DMSO-$d_6$) δ 1 1.15-10.83 (m, 1H), 8.78 (s, 1H), 8.69-8.58 (m, 1H), 8.07-7.76 (m, 4H), 7.76-7.59 (m, 4H), 7.42 (d, J=7.20 Hz, 3H), 7.26 (s, 1H), 3.84 (s, 2H), 2.79 (s, 3H). HRMS calcd for $C_{27}H_{23}N_5O_2$ (M+H)$^+$ 472.1749. found (M+H)$^+$ 472.1769.

1-(4-(2-Aminoacetamido)phenyl)-N-methyl-5-(phenanthren-2-yl)-1H-pyrazole-3-carboxamide (8). $^1$H NMR (300 MHz, DMSO-$d_6$) δ 8.70 (d, J=8.48 Hz, 2H), 8.00-7.86 (m, 2H), 7.78 (s, 1H), 7.66 (a, 5H), 7.50-7.42 (m, 1H), 7.38 (d, J=8.85 Hz, 2H), 7.13 (s, 1H), 3.86 (s, 2H), 2.97 (s, 3H). HRMS calcd for $C_{27}H_{23}N_5O_2$ (M-Na) 472.1749. found (M+Na)$^+$ 472.1731

2-Amino-N-(4-(3-(hydroxymethyl)-5-(phenanthren-2-yl)-1H-pyrazol-1-yl)phenyl)-acetamide (10). $^1$H NMR (300 MHz, DMSO-$d_6$) δ 8.87-8.70 (m, 2H), 7.98 (s, 2H), 7.91-7.73 (m, 2H), 7.72-7.55 (m, 5H), 7.45-7.34 (m, 2H), 7.28 (d, J=8.63 Hz, 2H), 6.76 (s, 1H), 4.54 (s, 2H), 3.88-3.71 (m, 2H). HRMS calcd for $C_{26}H_{22}N_4O_2$ (M+Na)$^+$ 455.1640. found (M+Na)$^+$ 455.1647.

3-Amino-N-(4-(3-(hydroxymethyl)-5-(phenanthren-3-yl)-1H-pyrazol-1-yl)phenyl)-propanamide (11). $^1$H NMR (300 MHz, DMSO-$d_6$) δ 8.86-8.69 (m, 1H), 8.66-8.47 (m, 1H), 7.92 (s, 4H), 7.75-7.58 (m, 4H), 7.53-7.33 (m, 1H), 7.29-7.15 (m, 2H), 6.83 (s, 1H), 4.55 (s, 2H), 3.12-2.98 (m, 2H), 2.86-2.63 (m, 2H). HRMS calcd for $C_{27}H_{24}N_4O_2$ (M+H)$^+$ 437.1978. found (M+H)$^+$ 437.1956.

3-Amino-N-(4-(3-(hydroxymethyl)-5-(phenanthren-2-yl)-1H-pyrazol-1-yl)phenyl)-propanamide (12). $^1$H NMR (300 MHz, DMSO-$d_6$) δ 8.88-8.70 (m, 2H), 7.98 (s, 2H), 7.92-7.73 (m, 2H), 7.61 (d, J=8.49 Hz, 4H), 7.45-7.33 (m, 1H), 7.26 (s, 2H), 6.75 (s, 1H), 4.54 (s, 2H), 3.13-2.98 (m, 2H), 2.71 (m, 2H). HRMS calcd for $C_{27}H_{24}N_4O_2$ (M+Na)$^+$ 459.1797. found (M+Na)$^+$ 459.1794.

1-(4-(3-Aminopropanamido) phenyl)-N-methyl-5-(phenanthren-3-yl)-1H-pyrazole-3-carboxamide (13). $^1$H NMR (300 MHz, DMSO-$d_6$) δ 8.84-8.72 (m, 1H), 8.69-8.58 (m, 1H), 7.95-7.75 (m, 4H), 7.67 (s, 4H), 7.38-7.30 (m, 3H), 7.25 (s, 1H), 3.10-2.95 (m, 2H), 2.76 (s, 3H), 2.76-2.71 (m, 2H). HRMS calcd for $C_{28}H_{25}NO_2$ (M+Na)$^+$ 486.1906. found 486.1922.

1-(4-(3-aminopropanamido) phenyl)-N-methyl-5-(phenanthren-2-yl)-1 μl-pyrazole-3-carboxamide (14). $^1$H NMR (300 MHz, DMSO-$d_6$) δ 8.77 (s, 2H), 8.03 (s, 2H), 7.92-7.73 (m, 2H), 7.67 (d, J=8.42 Hz, 4H), 7.35 (d, J=8.42 Hz, 3H), 7.15 (s, 1H), 3.06-3.00 (d, J=6.2 Hz, 2H), 2.79 (d, J=4.30 Hz, 3H), 2.74 (d, J=6.2 Hz, 2H). HRMS calcd for $C_{28}H_{25}N_5O_2$ (M+H)$^+$ 464.2087. found (M+H)$^+$ 404.2087.

(1-(4-Aminophenyl)-5-(phenanthren-3-yl)-1H-pyrazol-3-yl)methanol (16). $^1$H NMR (300 MHz, DMSO-$d_6$) δ 8.72-8.61 (m, 1H), 8.58-8.48 (m, 1H), 8.00-7.94 (m, 1H), 7.92-7.87 (m, 1H), 7.87-7.75 (m, 2H), 7.69-7.61 (m, 2H), 7.46-7.41 (m, 1H), 7.00-6.93 (m, 2H), 6.56-6.48 (m, 2H), 6.80-6.75 (m, 1H), 4.58-4.44 (m, 2H). HRMS calcd for $C_{24}H_{21}N_3O$ (M+Na)$^+$ 388.1426. found 388.1428.

1-(4-Aminophenyl)-N-methyl-5-(phenanthren-3-yl)-1H-pyrazole-3-carboxamide (17). $^1$H NMR (300 MHz, DMSO-$d_6$) δ 8.70-8.63 (m, 1H), 8.58-8.48 (m, 1H), 8.00-7.93 (m, 1H), 7.93-7.87 (m, 1H), 7.87-7.75 (m, 2H), 7.69-7.59 (m, 2H), 7.48-7.42 (m, 1H), 7.19-7.15 (m, 1H), 7.07-6.99 (m, 2H), 6.60-6.51 (m, 2H), 2.82-2.74 (m, 3H). HRMS calcd for $C_{25}H_{22}N_4O$ (M+Na)$^+$ 415.1535. found 415.1550.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds are effective, the inventors are not bound by theories described herein. The invention is not limited to the exact details shown and described, for variations obvious to one skilled in the art will be included within the invention defined by the claims.

What is claimed is:

1. A compound according to formula I:

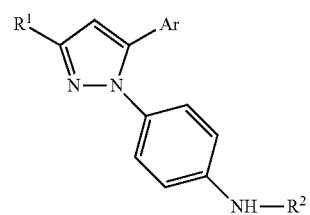

wherein Ar is 3-phenanthrene, $R^1$ is selected from —C(=O)NH-isopropyl and $CF_3$ and $R^2$ is selected from —C(=O)CH$_2$NH$_2$ and —C(=O)CH$_2$CH$_2$NH$_2$, and pharmaceutically acceptable salts thereof.

2. A method of treating PAK-dependent cancer by administering to a subject a therapeutically effective amount of a compound according to formula I:

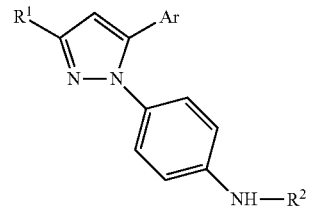

wherein Ar is 3-phenanthrene, $R^1$ is selected from —C(=O)NH-isopropyl and $CF_3$ and $R^2$ is selected from —C(=O)CH$_2$NH$_2$ and —C(=O)CH$_2$CH$_2$NH$_2$, and pharmaceutically acceptable salts thereof.

3. The method of claim 2, wherein the cancer is breast cancer.

4. The method of claim 2, wherein the cancer is thyroid cancer.

5. A method of inhibiting one or more p21-activated kinases in a subject by administering an effective amount of a compound according to formula I:

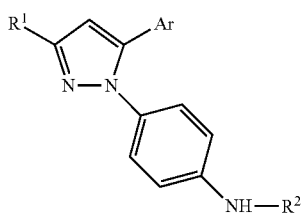

wherein Ar is 3-phenanthrene, R$^1$ is selected from —C(=O)NH-isopropyl and CF$_3$ and R$^2$ is selected from —C(=O)CH$_2$NH$_2$ and —C(=O)CH$_2$CH$_2$NH$_2$, and pharmaceutically acceptable salts thereof.

6. The method of claim 5, wherein a plurality of p21-activated kinases are inhibited.

7. The method of claim 5, wherein the p21-activated kinases comprise PAK1.

8. The method of claim 5, wherein the compound does not substantially inhibit phosphoinositide-dependent kinase-1.

9. The compound of claim 1, wherein the compound has the structure

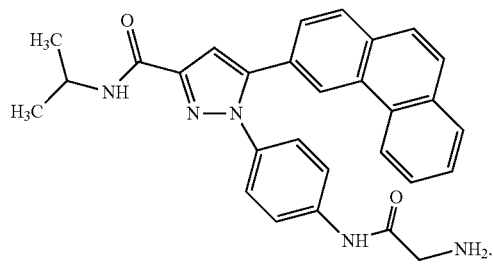 [SMILES: CC(C)NC(=O)c1cc(-c2ccc3ccc4ccccc4c3c2)n(-c2ccc(NC(=O)CN)cc2)n1]

10. The compound of claim 1, wherein the compound has the structure

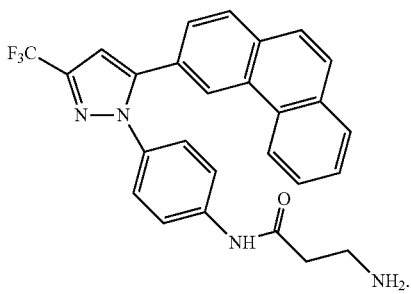 [SMILES: NCCC(=O)Nc1ccc(-n2nc(C(F)(F)F)cc2-c2ccc3ccc4ccccc4c3c2)cc1]

* * * * *